United States Patent
Shan et al.

(10) Patent No.: US 12,096,939 B2
(45) Date of Patent: Sep. 24, 2024

(54) FIRING MECHANISM AND STAPLER

(71) Applicant: TOUCHSTONE INTERNATIONAL MEDICAL SCIENCE CO., LTD., Jiangsu (CN)

(72) Inventors: Teng Shan, Jiangsu (CN); Yuanyang Cao, Jiangsu (CN); Xueqian Huang, Jiangsu (CN)

(73) Assignee: TOUCHSTONE INTERNATIONAL MEDICAL SCIENCE CO., LTD., Jiangsu (CN)

( * ) Notice: Subject to any disclaimer, the term of this patent is extended or adjusted under 35 U.S.C. 154(b) by 566 days.

(21) Appl. No.: 17/311,215

(22) PCT Filed: Dec. 20, 2019

(86) PCT No.: PCT/CN2019/127100
§ 371 (c)(1),
(2) Date: Jun. 4, 2021

(87) PCT Pub. No.: WO2020/125765
PCT Pub. Date: Jun. 25, 2020

(65) Prior Publication Data
US 2022/0031330 A1    Feb. 3, 2022

(30) Foreign Application Priority Data

Dec. 20, 2018  (CN) .......................... 201811563035.0
Dec. 20, 2018  (CN) .......................... 201822152931.X
Feb. 2, 2019   (CN) .......................... 201920187434.5

(51) Int. Cl.
*A61B 17/072* (2006.01)
*A61B 17/00* (2006.01)
(Continued)

(52) U.S. Cl.
CPC ........ *A61B 17/1155* (2013.01); *A61B 17/072* (2013.01); *A61B 2017/00367* (2013.01); *A61B 2017/0042* (2013.01); *A61B 2090/035* (2016.02)

(58) Field of Classification Search
CPC .............. A61B 17/1155; A61B 17/072; A61B 17/07207; A61B 2090/035; A61B 2017/042; A61B 2017/00367
(Continued)

(56) References Cited

U.S. PATENT DOCUMENTS 5,403,312 A  *  4/1995  Yates ................. A61B 18/1206
                                                    606/49
5,597,107 A      1/1997  Knodel et al.
(Continued)

FOREIGN PATENT DOCUMENTS

CN    2383477   Y     6/2000
CN    104224260 A  * 12/2014    ........... A61B 17/072
(Continued)

OTHER PUBLICATIONS

Office Action regarding corresponding EP App. No. 19 900 141.3; issued Oct. 13, 2023.
(Continued)

*Primary Examiner* — Joshua G Kotis
(74) *Attorney, Agent, or Firm* — Dickinson Wright PLLC

(57) ABSTRACT

A firing mechanism and a circular stapler are provided. The firing mechanism includes a staple pushing assembly, which includes an actuating rod provided with a stopping groove; a firing handle, wherein a pin post is provided in the firing handle, a first end of the pin post is capable of protruding from a first end of the firing handle and entering the stopping groove, to stop the firing handle from rotating relative to the actuating rod; and a pressing button capable of moving
(Continued)

along a first direction to press the first end of the pin post to move towards a second end of the firing handle. Before the stapler reaches a ready-to-fire state, the pin post is inserted in the stopping groove of the actuating rod, to limit the rotation of the firing handle, therefore the operator cannot press the firing handle to fire the stapler.

7 Claims, 22 Drawing Sheets

(51) Int. Cl.
    *A61B 17/115*     (2006.01)
    *A61B 90/00*     (2016.01)
(58) Field of Classification Search
    USPC ........................................................ 227/175.2
    See application file for complete search history.

(56) References Cited

U.S. PATENT DOCUMENTS

| | | | |
|---|---|---|---|
| 10,905,415 B2 * | 2/2021 | DiNardo | A61B 17/1155 |
| 2008/0314958 A1 * | 12/2008 | Scirica | A61B 17/07207 |
| | | | 227/179.1 |
| 2013/0092719 A1 * | 4/2013 | Kostrzewski | A61B 17/105 |
| | | | 227/177.1 |
| 2015/0136833 A1 | 5/2015 | Shelton | |
| 2015/0297216 A1 * | 10/2015 | Williams | A61B 17/07207 |
| | | | 227/175.2 |

FOREIGN PATENT DOCUMENTS

| | | |
|---|---|---|
| CN | 104224260 B | 8/2016 |
| CN | 104586452 B | 1/2017 |
| CN | 206641873 U | 11/2017 |
| CN | 108403176 A | 8/2018 |
| CN | 209529241 U | 10/2019 |
| CN | 209644987 U | 11/2019 |
| EP | 2090251 A2 | 8/2009 |
| JP | 2009189832 A | 8/2009 |
| JP | 2018508278 A | 3/2018 |
| RU | 145252 U1 | 9/2014 |

OTHER PUBLICATIONS

English translation of First Office Action regarding corresponding JP App. No. 2021-535931; issued May 31, 2022.
First Office Action regarding corresponding RU App. No. 2021118185/14; dated Mar. 16, 2022.
Partial Supplemental European Search Report regarding corresponding EP App. No. 19900141.3; dated Jan. 10, 2022.
Extended European Search Report regarding corresponding EP App. No. 19900141.3; dated Mar. 25, 2022.
International Search Report regarding corresponding App. No. PCT/CN2019/127100; dated Mar. 20, 2020.

* cited by examiner

FIRING MECHANISM AND STAPLER

CROSS-REFERENCE TO RELATED APPLICATIONS

This application is based upon PCT patent application No. PCT/CN2019/127100, filed on Dec. 20, 2019, which claims priority to Chinese Patent Application No. 201822152931.X, filed on Dec. 20, 2018, and Chinese Patent Application No. 201811563035.0, filed on Dec. 20, 2018, and Chinese Patent Application No. 201920187434.5, filed on Feb. 2, 2019, the entire contents of which are incorporated herein reference.

TECHNICAL FIELD

The present disclosure relates to medical instruments technology, more particularly, to a firing mechanism and a stapler.

BACKGROUND

Digestive tract tumor is one of human diseases of high incidence. During treatment, a stapler is widely used for suturing physiological tissues such as tissues in the digestive tract, instead of the manual operation by doctors. Linear stapler is a common surgical instrument in a way of linear stapling, and used for suturing tissues in esophagus, stomach, intestinal tract etc. during operation.

The linear stapler generally includes an instrument body and a head portion detachably mounted at the instrument body. The head portion can pass through small incision on body through a trocar, to get close to surgical site to perform the operation. Specifically, the instrument body includes a firing handle, the detachable head portion includes a staple box housing and a staple head portion mounted at a distal end of the staple box housing. A firing assembly is provided in the staple box housing, and the staple head portion is configured to cut and suture tissues. Driven by the firing handle, the firing assembly can drive the staple head portion to complete the cutting and suturing operation.

In the existing linear stapler, before the operation is prepared, the doctor may mistakenly press the firing handle for the sake of being careless or lack of experience, then the stapler will be fired mistakenly. This will have a bad influence on the operation, and even cause damage to patients.

SUMMARY

To solve the problems in the prior art, the present disclosure provides a firing mechanism and a stapler, to realize that when a pin post is inserted into a stopping groove, the operator cannot press the firing handle to fire the stapler.

In a first aspect of the present disclosure, a firing mechanism for a stapler is provided, including: an actuating rod provided with a stopping groove; a firing handle, wherein a pin post is provided in the firing handle, a first end of the pin post is capable of protruding from a first end of the firing handle and entering the stopping groove, to stop the firing handle from rotating relative to the actuating rod; a pressing button capable of moving along a first direction to press the first end of the pin post to move towards a second end of the firing handle.

In some embodiments, the firing mechanism further includes a balance block, the balance block includes a rotating portion and a connecting portion, the connecting portion of the balance block is connected to the pressing button, and when the rotating portion of the balance block rotates, the pressing button is driven to move.

In some embodiments, a pin groove for accommodating the pin post is provided in the firing handle, and a reset component is provided between a second end of the pin post and the pin groove, so that the pin post is capable of moving in a straight line along a direction limited by the pin groove.

In some embodiments, the reset component is a compression spring.

In some embodiments, the pin post is provided with a first cooperating portion, and the pressing button is provided with a second cooperating portion; when the pressing button moves along a first direction, the first cooperating portion presses the second cooperating portion, so that the first end of the pin post moves towards the second end of the firing handle.

In some embodiments, the first cooperating portion is a boss including a stopping portion and a step portion, and the second cooperating portion is a concave platform.

In some embodiments, the pressing button includes a pressing portion connected to the second cooperating portion, and the pressing portion passes through a housing of the stapler.

In some embodiments, a limiting component for the pressing button is provided at a housing of the stapler, and the limiting component is located on a route of the pressing button moving along the first direction.

In some embodiments, a proximal end of the stopping groove is provided with an arc groove concave towards an inside portion of the actuating rod.

In some embodiments, the firing handle is further provided with a driving component, a gear rack is provided at a proximal end side of the stopping groove, and a pushing tooth is provided at a distal end side of the stopping groove; when the driving component is in contact with the pushing tooth, the driving component is capable of pushing the actuating rod to move towards a distal end of the stapler.

In a second aspect of the present disclosure, a firing mechanism for a stapler, wherein, the firing mechanism includes: an actuating rod provided with a stopping groove; a firing handle, wherein a pin post is provided in the firing handle, a first end of the pin post is capable of protruding from the firing handle and entering the stopping groove, to stop the firing handle from rotating relative to the actuating rod; a button assembly including a pressing rod, wherein a first end of the pressing rod is inserted in the firing handle; the pressing rod is capable of further entering the firing handle, to press the first end of the pin post to move towards a second end of the firing handle.

In some embodiments, the pin post is provided with a first cooperating portion, and the first cooperating portion has a first inclined surface; a first end of the pressing rod is provided with a second cooperating portion, and the second cooperating portion has a third inclined surface; when the pressing rod is in its initial position, the third inclined surface fits with the first inclined surface.

In some embodiments, the first cooperating portion further has a second inclined surface located correspondingly to the first inclined surface, and the second cooperating portion further has a fourth inclined surface located correspondingly to the third inclined surface; when the pressing rod is in its initial position, the fourth inclined surface fits with the second inclined surface.

In some embodiments, an intersection between the first inclined surface and the second inclined surface protrudes towards the first end of the pin post, a cavity is formed at an intersection between the third inclined surface and the fourth inclined surface; and the intersection between the first inclined surface and the second inclined surface enters the cavity.

In some embodiments, a pin groove for accommodating the pin post and a pressing rod guiding groove for accommodating the pressing rod are respectively provided in the firing handle, the pin groove extends along a third direction, and the pressing rod guiding groove extends along a second direction.

In some embodiments, the button assembly further includes a connecting portion and a guiding rod, the guiding rod is connected to the pressing rod through the connecting portion; a button guiding groove for accommodating the guiding rod is further provided in the firing handle, and a first end of the guiding rod is inserted in the button guiding groove.

In some embodiments, a sliding groove is further provided on a side of the button guiding groove, a clamping portion is provided at the first end of the guiding rod, and the clamping portion is accommodated in the sliding groove.

In some embodiments, the button assembly further includes a connecting portion and a button shaft, and the button shaft is connected to the pressing rod through the connecting portion.

In some embodiments, a mounting groove for accommodating the button shaft is further provided in the firing handle, and a returning spring for the button assembly is provided in the mounting groove.

In some embodiments, a pin groove for accommodating the pin post is provided in the firing handle, and a reset component is provided between a second end of the pin post and the pin groove, so that the pin post is capable of moving in a straight line along a direction limited by the pin groove.

In a third aspect of the present disclosure, a circular stapler is provided, including the firing mechanism according to the first aspect or the second aspect of the present disclosure.

The firing mechanism and the circular stapler has the following advantages.

The present disclosure provides a firing mechanism for a stapler. The cooperation between the pin post and the actuating rod realizes the firing insurance mechanism of the stapler. After the stapler is closed, the doctor needs to adjust the clamping state of the tissues in the staple head portion, for example flattens the tissues, to make the tissues to reach a ready-to-fire state. Before the tissues reach the ready-to-fire state, the pin post is inserted in the stopping groove of the actuating rod, to limit the rotation of the firing handle, then the driving component of the firing handle cannot push the actuating rod to move towards the actuating rod. The operator cannot press the firing handle to fire the stapler, to prevent the stapler from being fired before the operation is prepared. When the button assembly moves along the first direction, the pin post can be pressed to separate from the stopping groove and will not limit the rotating action of the firing handle, the firing handle can be rotated, so the driving component can push the actuating rod to fire the stapler.

Besides, in another embodiment of the present disclosure, the position of the pin post can be switched by pressing the button assembly. The button assembly is provided at the firing handle and there is no need to specially provide a separate structure for carrying the button assembly, the doctor can operate the firing handle by only one hand, the button assembly is easy to operate, to facilitate the operation of the doctor.

The stapler of the present disclosure is not limited to a linear stapler, but also can be other kinds of stapler.

BRIEF DESCRIPTION OF THE DRAWINGS

Embodiments of the present disclosure will now be described, by way of example only, with reference to the accompanying schematic drawings. Apparently, the following figures are only exemplary. For the skilled in the art, other figures can also be gotten according to the following figures without creative work.

DETAILED DESCRIPTION

Figure 1:
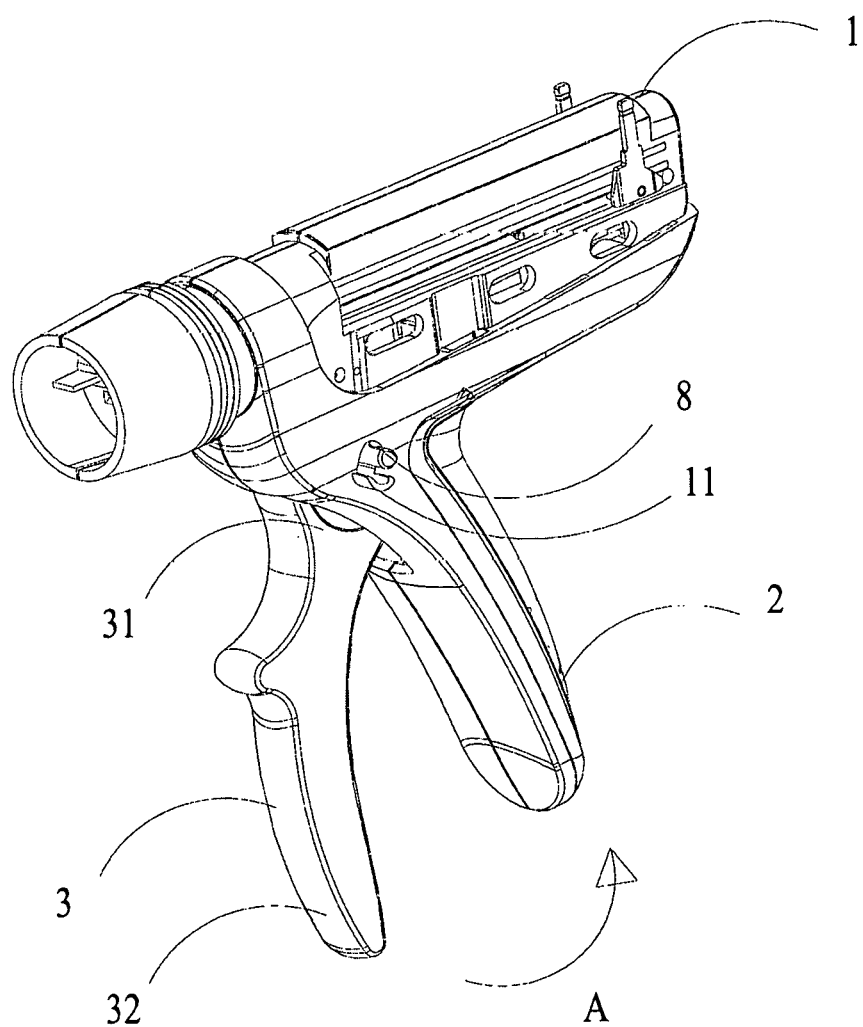
FIG. 1 is a structural schematic view of a firing mechanism cooperating with an instrument body according to an embodiment of the present disclosure.

Embodiments of the present disclosure will now be described, by way of example only, with reference to the accompanying schematic drawings according to embodiments of the present disclosure, to make the objective, technical proposal and advantages clearer. It should understand that the embodiment described are only a part of embodiments of the present disclosure, and are not intended to be a limitation to the protection scope of the present disclosure.

The present disclosure will be described in detail combining with the schematic drawings and the embodiments.

To solve the technical problem of the existing technology, the present disclosure provides a firing mechanism for a stapler. The firing mechanism includes an actuating rod provided with a stopping groove, a firing handle having a first position, and a pressing button. A pin post is provided in the firing handle, and the pin post has a first state and a second state. When the pin post is in the first state and the firing handle is in the first position, a first end of the pin post protrudes from a first end of the firing handle and enters the stopping groove, the firing handle cannot be rotated relative to the actuating rod to reset. When the pressing button moves along a first direction, the pressing button presses the first end of the pin post to move towards a second end of the firing handle, so that the pin post enters the second state from the first state. The present disclosure further provides a stapler including the firing mechanism. The stapler is not limited to a linear stapler, but also can be other kinds of stapler.

Therefore, in firing mechanism of the present disclosure, the cooperation between the pin post and the actuating rod realizes the firing insurance for the stapler. Before the stapler reaches the ready-to-fire state, the pin post is in the first state, and the pin post is inserted in the stopping groove on the actuating rod, to prevent the firing handle from rotating to reset. At this time, a driving component of the firing handle and the actuating rod cannot act on each other, even if the firing handle is pressed, the actuating rod cannot be pushed to move towards the distal end of the stapler, therefore, the operator cannot press the firing handle to fire the stapler, and mistaken firing of the stapler is prevented. Therefore, when the pin post is in the first state, the stapler is in the insurance state and cannot be fired normally. When moving along the first direction, the press button presses the pin post to move away from the stopping groove, then the pin post no longer prevents the firing handle from rotating.

The structure of the firing mechanism in each embodiment will be described in the following combining with the schematic drawings.

FIGS. 1-12 are structural schematic views of a firing mechanism and the components thereof according to a first embodiment of the present disclosure. In the embodiment, the firing mechanism includes an actuating rod 5, a firing handle 3 and a pressing button 8. The actuating rod 5 is provided with a stopping groove 53. The firing handle 3 has a first position and a second position. A pin post 6 having a first state and a second state is provided in the firing handle 3. When the pin post 6 is in the first state and the firing handle 3 is in the first position, a first end 61 of the pin post 6 protrudes from a first end 31 of the firing handle 3 and enters the stopping groove 53, the firing handle 3 cannot be rotated relative to the actuating rod 5. When the pressing button 8 moves along the first direction, the pressing button 8 presses the first end 61 of the pin post 6 to move towards a second end 32 of the firing handle 3, so that the pin post 6 enters the second state from the first state. In the embodiment, the first direction is a direction B shown in FIG. 4. In the embodiment, when the pin post 6 is in the second state, the pin post 6 retracts towards the second end 32 of the firing handle 3 to separate from the stopping groove 53.

FIG. 1 is a schematic view of the firing mechanism cooperating with the instrument body of the embodiment. The actuating rod 5 is provided in the instrument body 1, and a distal end of the actuating rod 5 is connected to a cutter pushing assembly. The actuating rod 5 has a third position and a fourth position, wherein the third position is at a proximal end side of the fourth position. When the actuating rod 5 moves from the fourth position towards the distal end of the stapler, the cutter pushing assembly can be pushed to fire the stapler. The instrument body 1 is provided with a fixed handle 2, the first end 31 of the firing handle 3 is rotatably connected to the instrument body 1, and a reset component for the firing handle 3 is provided between the firing handle 3 and the instrument body 1. The reset component for the firing handle 3 can be a tension spring, a torsion spring, a compression spring etc. When pressed by an operator, the firing handle 3 can move along a direction A shown in FIG. 1 relative to the instrument body 1. The position of the firing handle 3 shown in FIG. 1 is the second position, at this time, the firing mechanism is in the initial state. When the operator presses the firing handle 3, and the second end 32 of the firing handle 3 rotates towards the fixed handle 2, the firing handle 3 enters the first position. When the operator releases the firing handle 3, the firing handle 3 can rotate along a direction opposite to the direction A under a function of the reset component for the firing handle 3, the second end 32 of the firing handle 3 rotates away from the fixed handle 2, and the firing handle 3 returns to the second position.

In the present disclosure, positions of the distal end and the proximal end are defined relative to an operator, wherein, the proximal end is an end closer to the operator, the distal end is another end far from the operator and closer to a surgical position. For example, in the viewpoint of FIG. 1, a distal end of the instrument body 1 is the left end, and a proximal end of the instruments body 1 is the right end.

Figure 2:
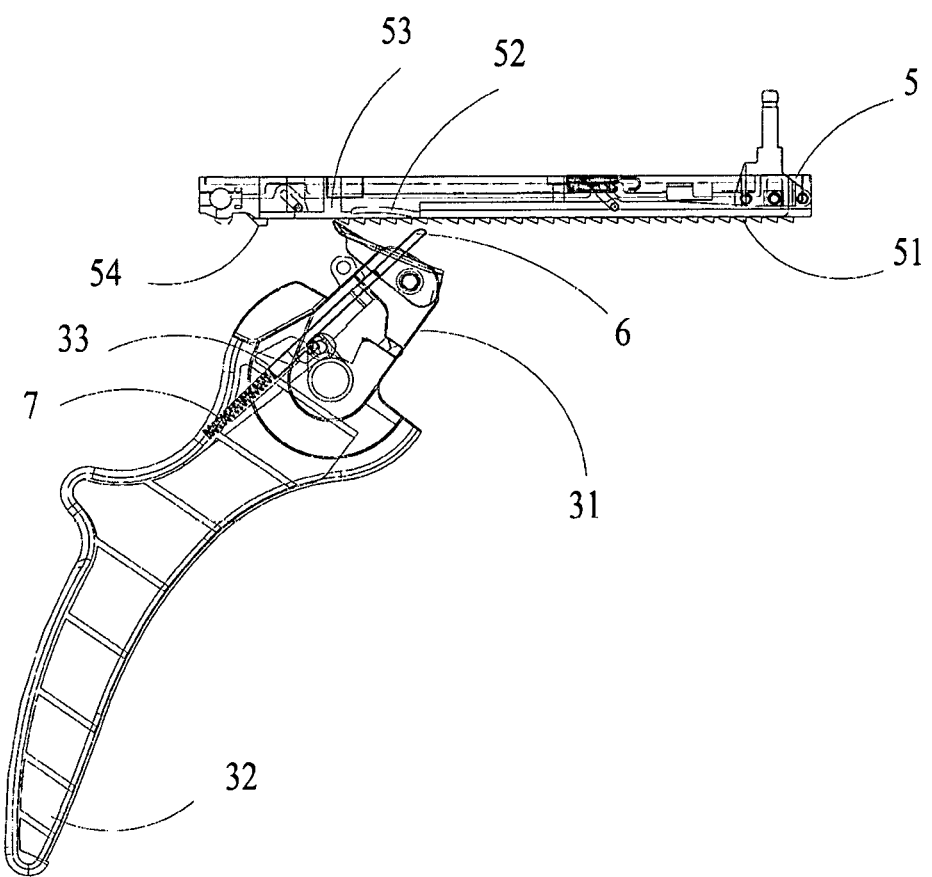
FIG. 2 is a structural schematic view of the firing mechanism in an initial state according to an embodiment of the present disclosure.
Figure 3:
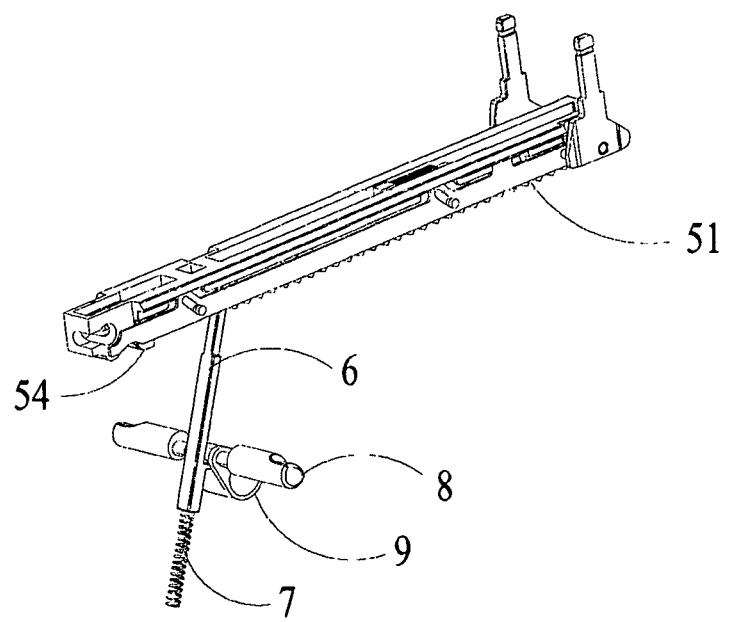
FIGS. 3-4 are schematic views of a pin post cooperating with a pressing button and a gear rack according to an embodiment of the present disclosure.

FIG. 2 is a structural schematic view of the firing mechanism in the initial state according to the embodiment of the present disclosure. At this time, the firing handle 3 is in the second position, and the pin post 6 is in the first state. In the embodiment, a pin groove 33 is provided in the firing handle 3, and the pin post 6 is located in the pin groove 33. The pin post 6 can only move along a direction limited by the pin groove 33, and a reset component 7 for the pin post 6 is provided between a second end 62 of the pin post 6 and the pin groove 33. In the embodiment, the reset component 7 for the pin post 6 is a compression spring. When the pin post 6 is under a pressure from the pressing button 8 along a direction towards the second end 32 of the firing handle 3, the pin post 6 enters the second state from the first state. At the same time, the second end 62 of the pin post 6 presses the compression spring to deform. That is, the first state of the pin post 6 is a protruding state, the second state of the pin post is a retracting state. When the pressing button 8 moves along the direction opposite to the first direction, the pressing button 8 no longer presses the pin post 6, then the pin post 6 returns to the first state under the deformation returning force of the compression spring.

As shown in FIGS. 3-6, in the embodiment, the firing mechanism further includes a balance block 9. The balance block 9 includes a rotating portion 91 and a connecting portion 92, the connecting portion 92 of the balance block 9 is fixedly connected to the pressing button 8, and the rotating portion 91 is rotatably connected to the fixed handle 2. When the rotating portion 91 rotates along the first direction, the pressing button 8 is driven to move along the first direction. The balance block 9 can also be rotatably connected to a housing of the instrument body 1. For example, a rotating shaft is provided in the housing of the instrument body 1, and the balance block 9 is sheathed outside the rotating shaft. The present disclosure is not limited to this, in other alternative embodiments, the balance block 9 can also use other kinds of fixing structure.

Therefore, in the embodiment, with the cooperation among the balance block 9, the pressing button 8 and the pin post 6, the movement of the pressing button 8 can switch the state of the pin post 6. When moving, the pressing button 8 always moves around the balance block 9, and the pressing button 8 has no displacement along an axial direction of the balance block 9, relative to the instrument body 1. Therefore, the structural stability of the whole firing mechanism is improved, and the firing mechanism is more convenient to use for the operator.

As shown in FIGS. 3-6, in the embodiment, a first cooperating portion 63 and a second cooperating portion 81 are respectively provided at the pin post 6 and the pressing button 8. When the pressing button 8 moves along the first direction, the first cooperating portion 63 presses the second cooperating portion 81, so that the first end 61 of the pin post 6 moves towards the second end 32 of the firing handle 3.

Figure 4:
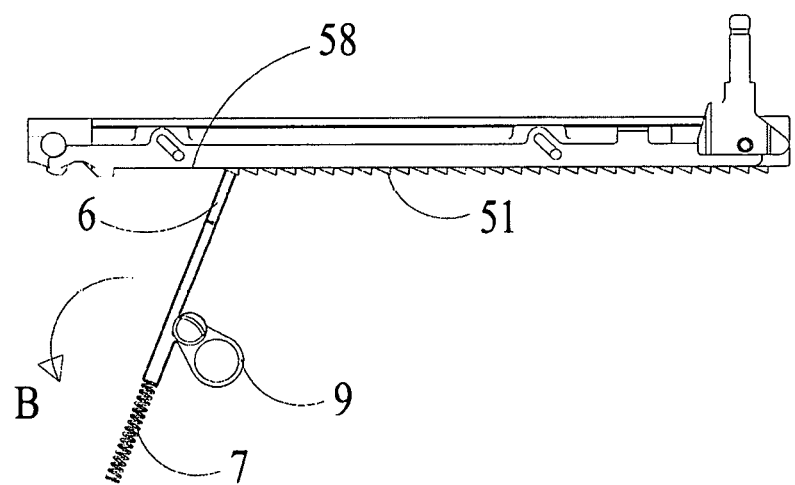
Figure 5:
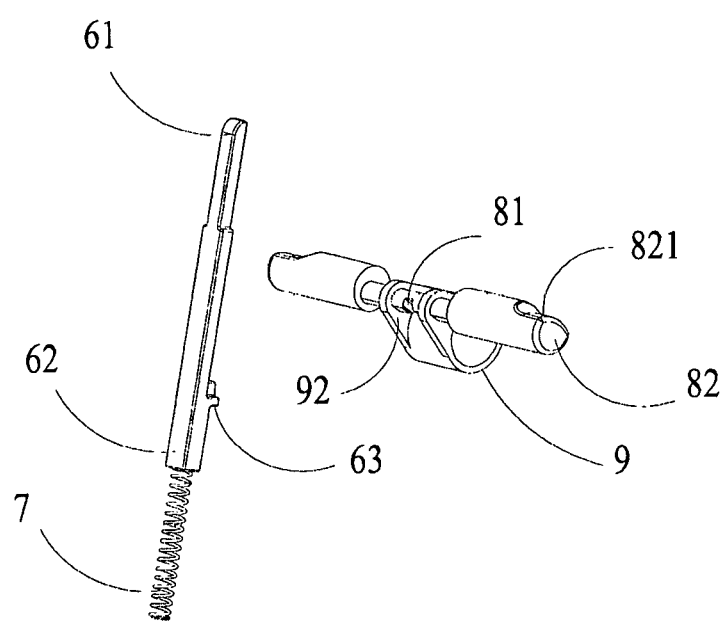
FIGS. 5-6 are schematic views of the pin post cooperating with the pressing button according to an embodiment of the present disclosure.
Figure 6:
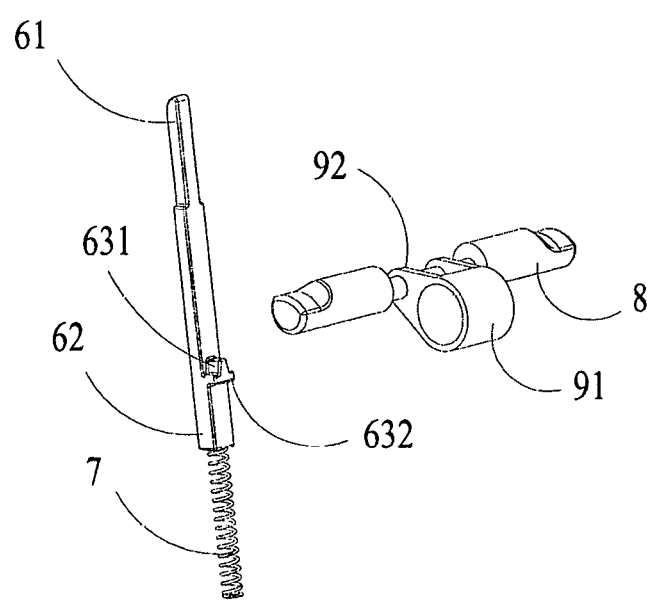

In the embodiment, the first cooperating portion 63 is a boss having a stopping portion 631 and a step portion 632. The second cooperating portion 81 is a concave platform cooperated with the stopping portion 631. In the viewpoint of FIG. 4, the stopping portion 631 is disposed on top of the step portion 632, and the stopping portion 631 directly cooperates with the second cooperating portion 81. In an alternative embodiment, the first cooperating portion 63 can be a boss and the second cooperating portion 81 can also a boss. In another alternative embodiment, the first cooperating portion 63 can be a boss of other kind of shape, and the second cooperating portion 81 is a concave platform. In another alternative embodiment, the first cooperating portion 63 can be a concave platform, and the second cooperating portion 81 is a boss. The first cooperating portion 63 and the second cooperating portion 81 can also be other kinds of structures, which are all included in the protection scope of the present disclosure. When the balance block 9 rotates along the first direction, the pressing button 8 is driven to move along the first direction, the concave platform of the pressing button 8 presses the boss of the pin post 6, and presses the compression spring 7 along an inclined and downward direction, therefore, the first end 61 of the pin post 6 moves towards the second end 32 of the firing handle 3, and the pin post 6 enters the second state from the first state.

The pressing button 8 has a pressing portion 82 connected to the second cooperating portion 81. The pressing portion 82 passes through and protrudes from the housing of the stapler. In the embodiment, there are two pressing portions 82 respectively passing through two sides of the housing of the instrument body 1. Furthermore, the housing of the stapler is provided with a limiting component 11 for the pressing button 8, the limiting component 11 is located on a route of the pressing button 8 moving along the first direction, to limit the movement of the pressing button 8 along the first direction. Each pressing portion 82 is further provided with a finger position 821, so the operator can operate from either side of the housing conveniently.

Figure 7:
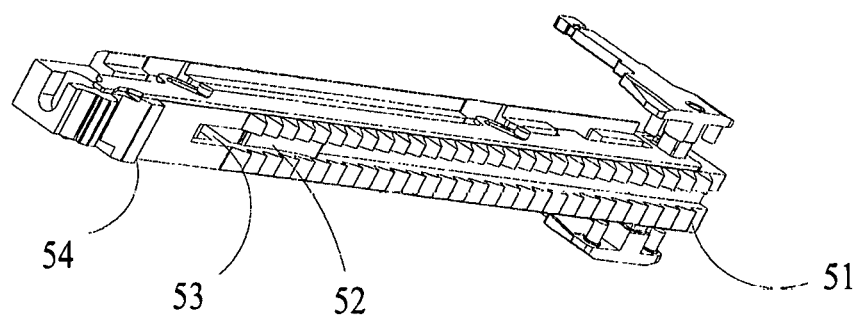
FIGS. 7-8 are structural schematic views of the gear rack according to an embodiment of the present disclosure.
Figure 8:
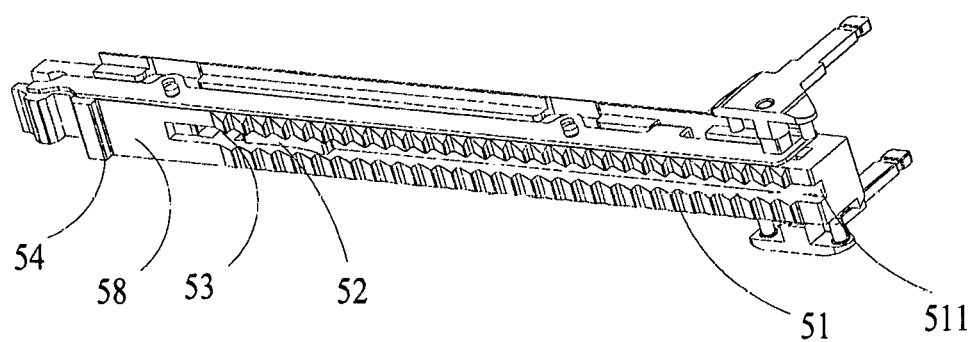
Figure 9:
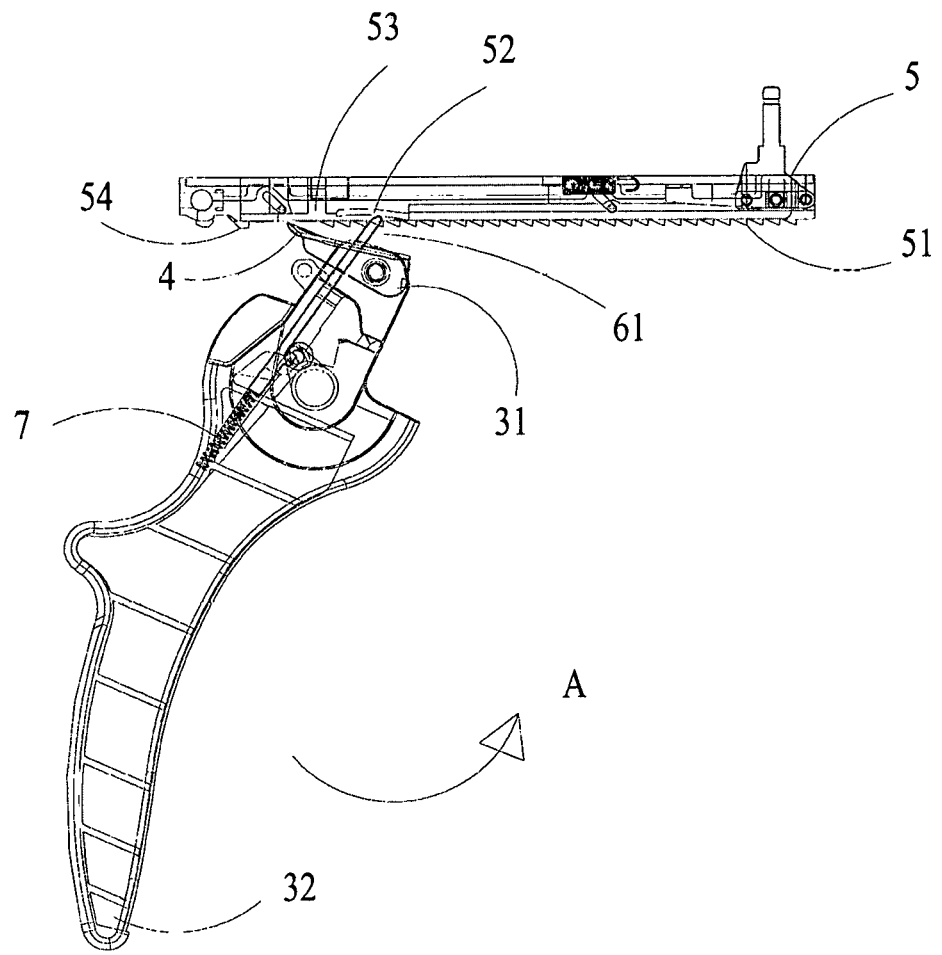
FIGS. 9-10 are structural schematic views of the firing mechanism when a firing handle is pressed according to an embodiment of the present disclosure.

As shown in FIG. 7 and FIG. 9, the proximal end of the stopping groove 53 is provided with an arc groove 52 concave towards an inside portion of the actuating rod 5. When the pin post 6 is in the first state and the firing handle 3 rotates from the second position to the first position, the arc groove 52 cooperates with the first end 61 of the pin post 6 and guides the first end 61 of the pin post 6 to enter the stopping groove 53.

In the embodiment, the firing handle 3 is further provided with a driving component 4, in the embodiment, the driving component 4 is a claw, and a lower portion of the actuating rod 5 is provided with a gear rack 51 and a pushing tooth 54. The gear rack 51 is located at a proximal end side of the pushing tooth 54, and a smooth portion 58 is provided between the gear rack 51 and the pushing tooth 54. The gear rack 51 and the pushing tooth 54 can respectively cooperates with the driving component 4 of the firing handle 3 in different states. In the initial state, the actuating rod 5 is located at the third position, when the firing handle 3 rotates from the second position towards the first position, the driving component 4 is in contact with the pushing tooth 54 and pushes the actuating rod 5 to move towards the distal end of the stapler to enter the fourth position. When the actuating rod 5 is in the fourth position and the firing handle 3 rotates from the second position towards the first position, the driving component 4 is in contact with the gear rack 51 and further pushes the actuating rod 5 to move towards the distal end of the stapler to push the cutter pushing assembly, therefore the stapler is fired.

In the following, the structures of the firing mechanism in different states of the embodiment are described in detail combining with FIGS. 9-12.

In the initial state, as shown in FIG. 2, the first end 61 of the pin post 6 protrudes from the firing handle 3, and is located at an area corresponding to the gear rack 51, the driving component 4 is located at the smooth portion 58.

Figure 10:
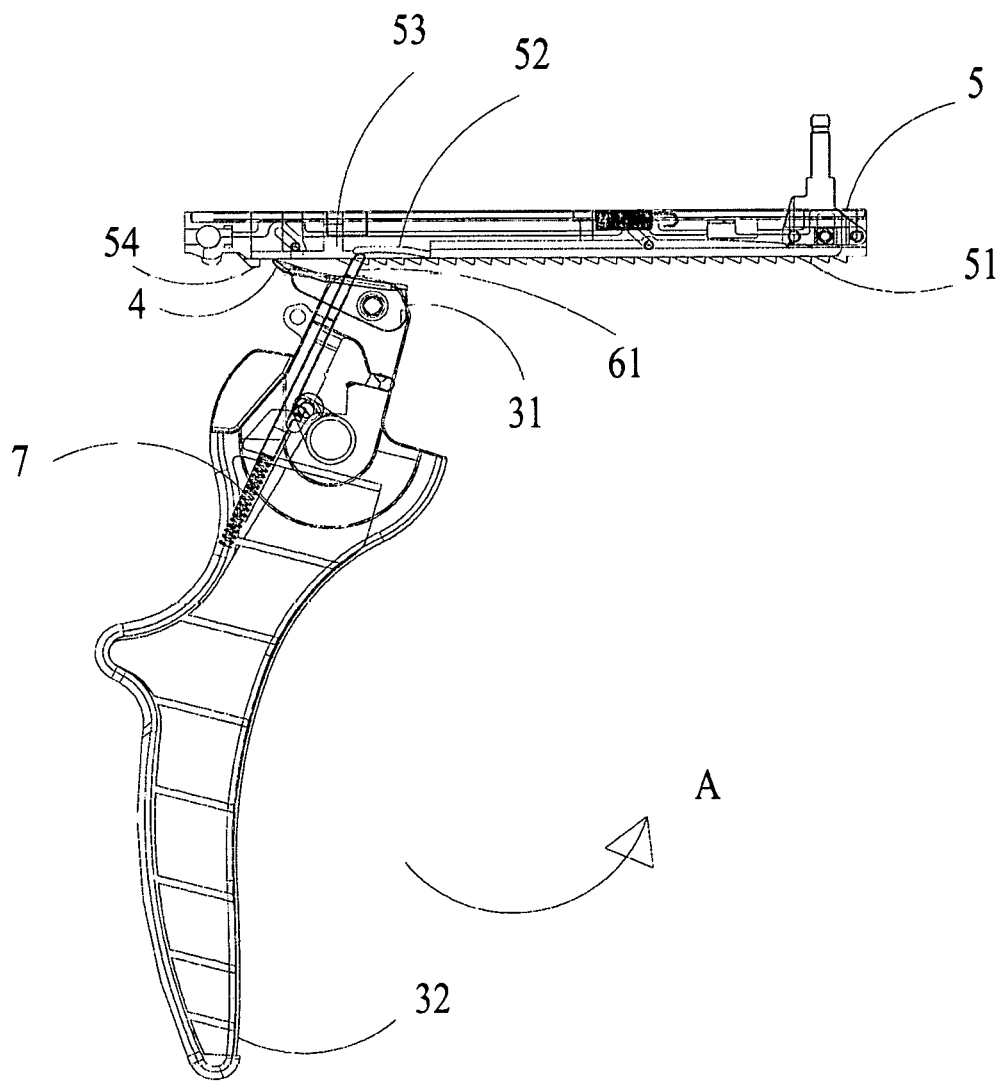
Figure 11:
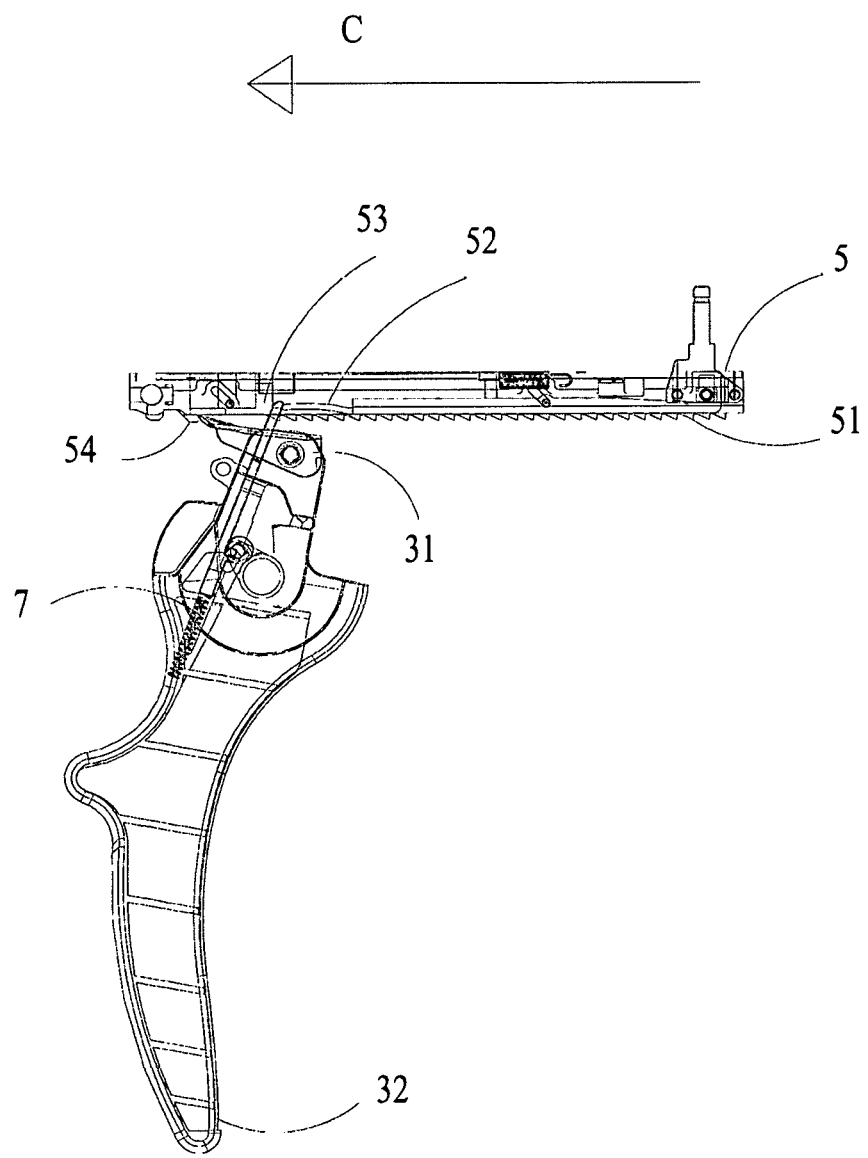
FIG. 11 is a structural schematic view of the firing mechanism at an insurance position according to an embodiment of the present disclosure.

FIG. 9 and FIG. 10 respectively show two positions of the firing handle 3 during rotating from the second position towards the first position when the firing handle 3 is pressed to close the stapler. During the process, the actuating rod 5 is driven to move from the third position to the fourth position. FIG. 9 shows a state when the firing handle 3 is pressed to a small extent, and the pin post 6 is in the first state. Although the pin post 6 is compressed to a small extent by the arc groove 52, the first end 61 of the pin post 6 still protrudes from the firing handle 3. FIG. 10 shows a state when the firing handle 3 is pressed to a maximum extent, the pin post 6 is still in the first state, and the pin post 6 already moves to the most distal end of the arc groove 52. That is, when the firing handle 3 rotates from the second position towards the first position, the first end 61 of the pin post 6 is guided by the arc groove 52 to gradually move towards the stopping groove 53. At this time, if the firing handle 3 continues to be pressed, as shown in FIG. 11, the firing handle 3 rotates towards the first position, and the driving component 4 comes to be in contact with the pushing tooth 54, if the firing handle 3 further continues to be pressed, the firing handle 3 can push the actuating rod 5 through the cooperation of the driving component 4 and the pushing tooth 54, to move towards the distal end of the stapler. The actuating rod 5 is pushed to move along a direction C and enters the fourth position, and the pin post 6 enters the stopping groove 53.

At this time, as the actuating rod 5 is pushed to the fourth position, if the firing handle 3 returns to the second position, the position of the driving component 4 will correspond to the position of the gear rack 51. When the operator continues pressing the firing handle 3 to move from the second position towards the first position, the driving component 4 will further push the gear rack 51 to move towards the distal end of the stapler, to fire the stapler. However, before the operation is prepared, if the operator mistakenly presses the firing handle 3, a mistaken firing of the stapler will happen. Therefore, in the embodiment, in the state shown in FIG. 10, as the first end 61 of the pin post 6 is inserted in the stopping groove 53, the stopping groove 53 limits the rotation of the pin post 6 and limits the rotation reset movement of the firing handle 3. The firing handle 3 cannot return to the second position from the first position shown in FIG. 11, and the operator cannot press the firing handle 3 again, so the mistaken firing before the operation is prepared is prevented.

In the state shown in FIG. 11, if the pressing button 8 is pressed downwards, the pressing button 8 rotates along the first direction, around the rotating portion 91 of the balance block 9, to drive the first end 61 of the pin post 6 to move towards the second end 32 of the firing handle 3. The first end 61 of the pin post 6 is separated from the stopping groove 53 of the actuating rod 5, so the stopping groove 53 no longer limits the rotation of the firing handle 3. At this time, if the operator releases the firing handle 3, the firing handle 3 can return to the second position under a reset function of the reset component for the firing handle 3, to enter the state shown in FIG. 12. After the firing handle 3 is reset, the pressing button 8 can be released, and the pin post 6 returns to the first state.

Figure 12:
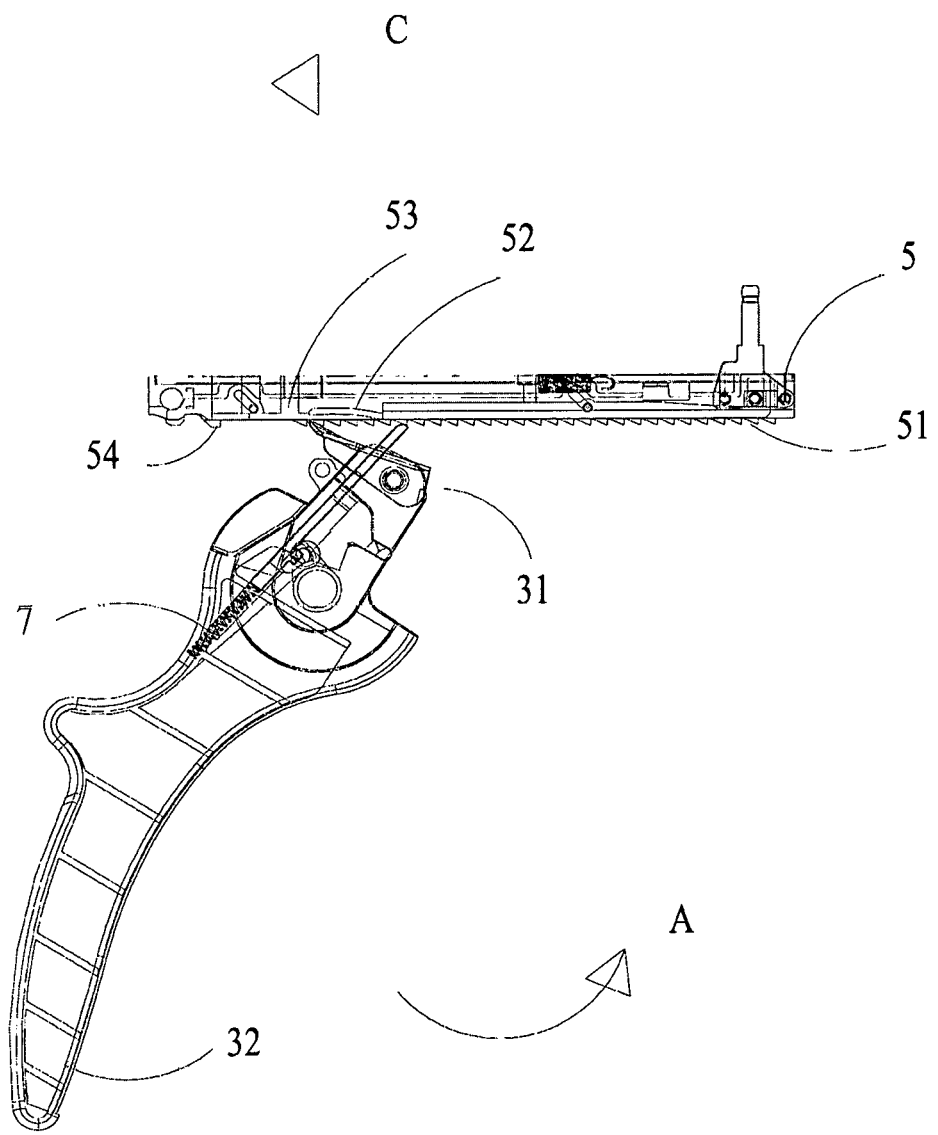
FIG. 12 is a structural schematic view of the firing mechanism at a ready-to-fire position according to an embodiment of the present disclosure.

FIG. 12 is a structural schematic view of the firing mechanism in the ready-to-fire position according to the embodiment. At this time, the actuating rod 5 is in the fourth position, and the driving component 4 of the firing handle 3 cooperates with the gear rack 51. If the firing handle 3 is pressed, the firing handle 3 rotates from the second position to the first position along the direction A. The driving component 4 will push the actuating rod 5 through the gear rack 51 to move towards the distal end of the stapler, to fire the stapler. To prevent that the first end 61 of the pin post 6 generates an excessive resistance to the rotation of the firing handle 3, a gear groove 511 is further provided in a portion of the gear rack 51 cooperated with the first end 61 of the pin post 6, so that the first end 61 of the pin post 6 can move towards the distal end of the gear rack 51 along the gear groove 511.

Another embodiment of the present disclosure provides a firing mechanism for a stapler. The firing mechanism includes an actuating rod, a firing handle, and a button assembly. An insurance pin post is provided in the firing handle. When the firing handle is pressed, the pin post enters a stopping groove provided on the actuating rod, so the firing handle cannot be rotated, and the stapler is in an insurance state at this time, to prevent the stapler from being fired mistakenly before the operation is prepared. The button assembly is provided at one side of the firing handle away from the fixed handle, and the button assembly can switch the states of the pin post through the cooperation between the button assembly and the pin post. After the operation is prepared, the doctor can press the button assembly towards the firing handle, so the button assembly presses the pin post to further enter an inside portion of the firing handle to separate from the stopping groove. Then the firing handle can be rotated normally, the stapler is in the ready-to-fire state, and the stapler can be fired normally by pressing the firing handle.

Another embodiment of the present disclosure provides a stapler including the above firing mechanism. The stapler can be prevented from being mistakenly fired before the operation is prepared, through the cooperation between the insurance pin post of the firing handle and the stopping groove of the actuating rod. The states of the pin post can be switched by the button assembly provided at the firing handle. When the button assembly is pressed, the stapler can be fired normally. The stapler is not limited to a linear stapler, but also can be other kinds of stapler, such as an arc stapler etc.

Figure 13:
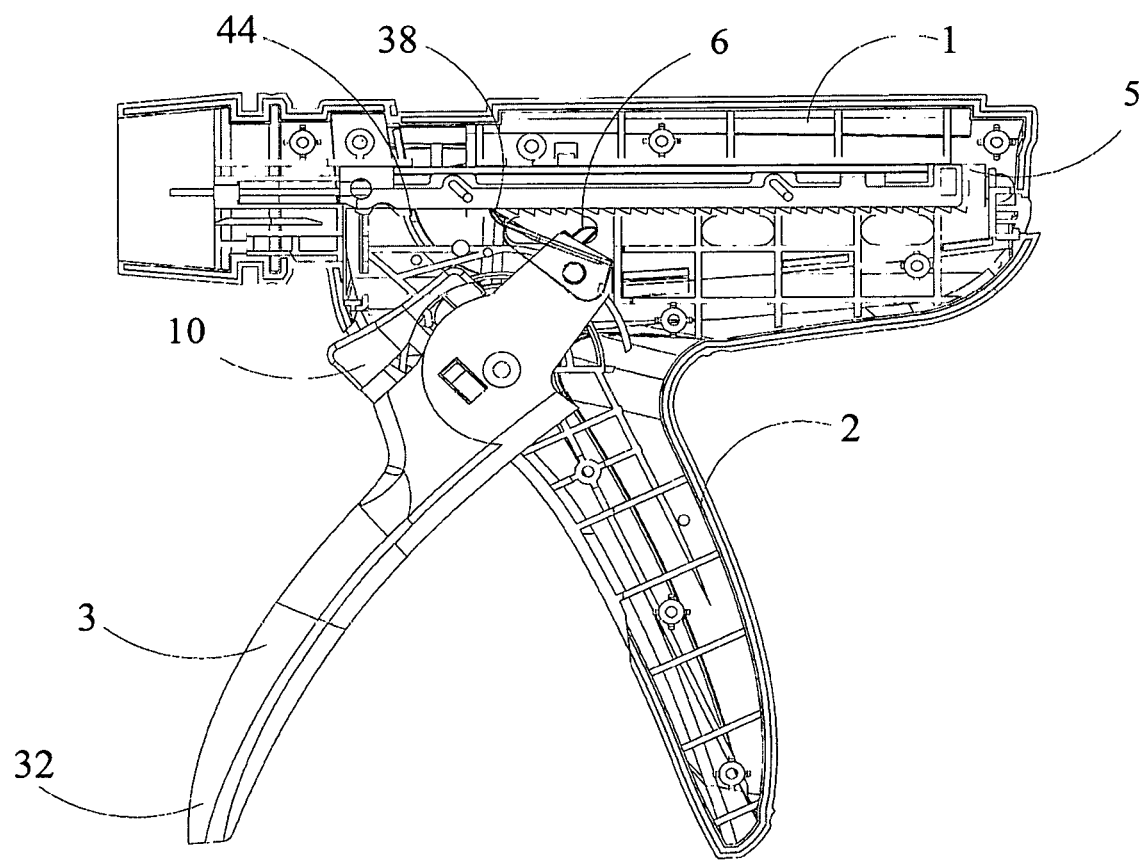
FIG. 13 is a structural schematic view of a firing mechanism according to another embodiment of the present disclosure.
Figure 14:
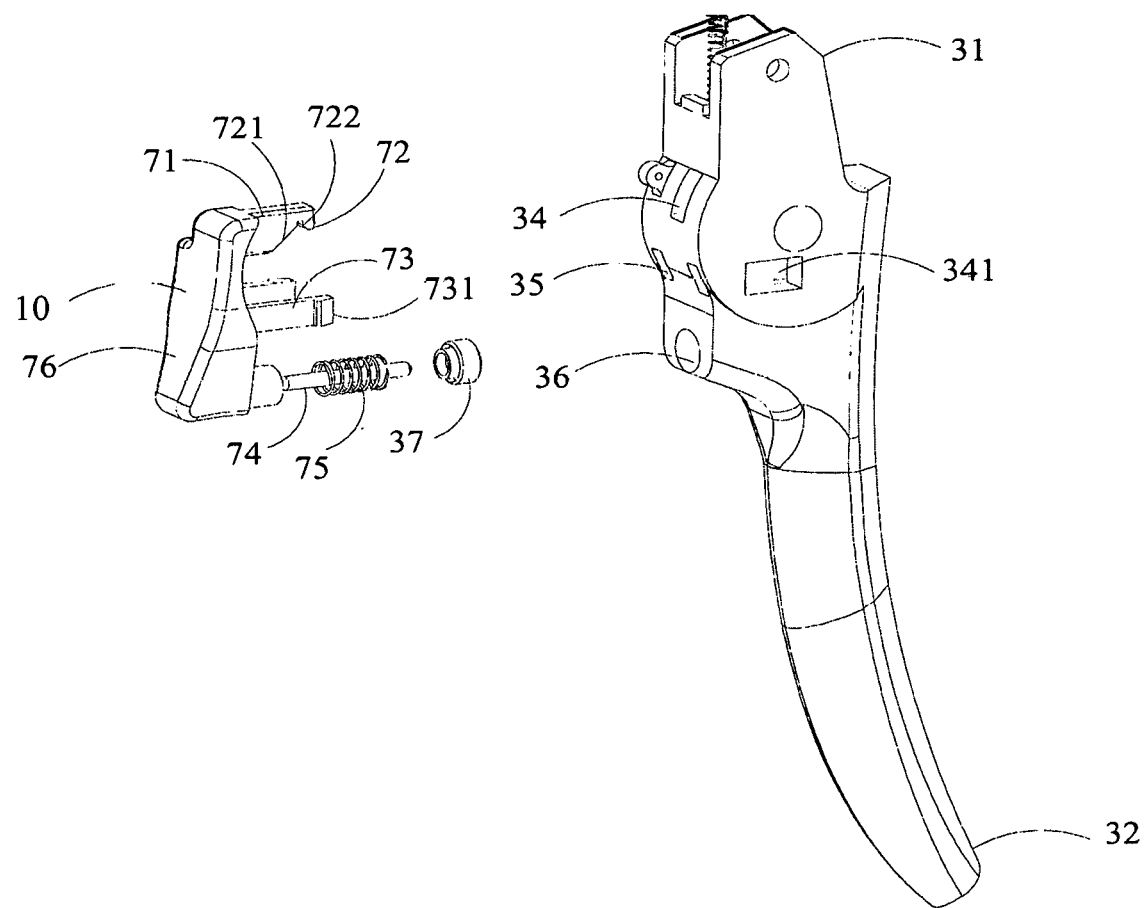
FIG. 14 is an exploded view of a firing handle and a button assembly according to another embodiment of the present disclosure.
Figure 15:
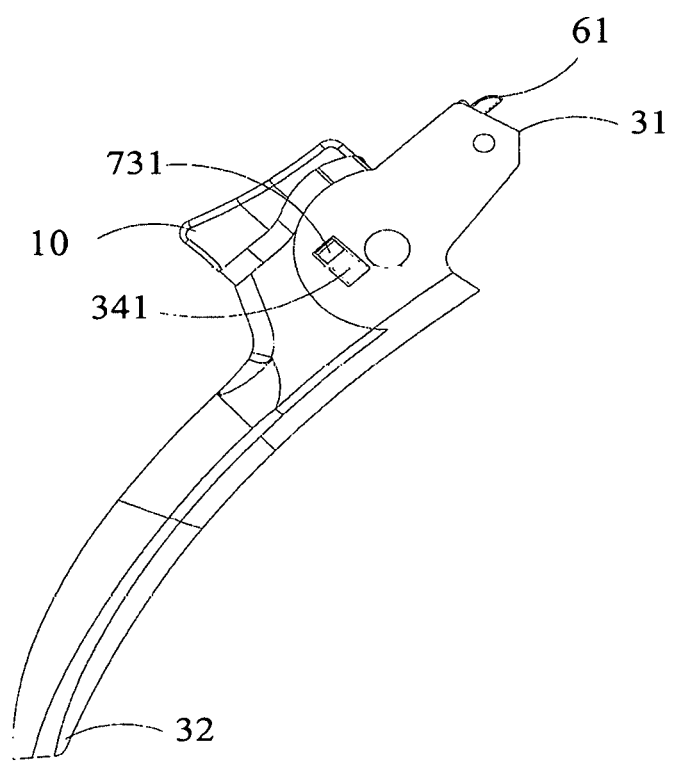
FIG. 15 is a structural schematic view of the firing handle cooperating with the button assembly according to another embodiment of the present disclosure.
Figure 16:
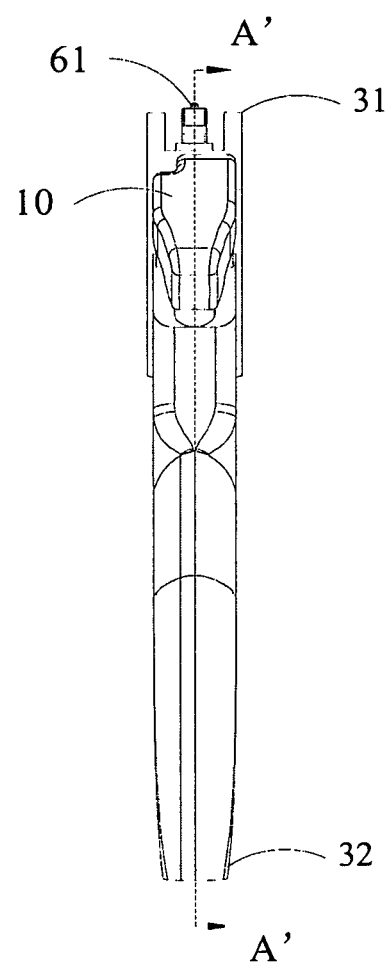
FIG. 16 is a side view of the firing handle cooperating with the button assembly according to another embodiment of the present disclosure.

The structure of the firing mechanism of another embodiment of the present disclosure will be further described in the following combining with FIGS. 13-22. FIG. 13 shows the structure of the firing mechanism cooperating with the stapler. As shown in FIG. 13, the firing handle is not pressed, and the button assembly is in its initial position. An actuating rod 5 is provided in the instrument body 1, a fixed handle 2 and a firing handle 3 are provided at one side of the instrument body 1. As shown in FIGS. 13-19, a stopping groove 53 is provided on the actuating rod 5, and a pin post 6 is provided in the firing handle 3. When the pin post 6 doesn't enter the stopping groove 53, the firing handle 3 can rotate relative to the fixed handle 2, towards or away from the fixed handle 2. In the initial state, the firing handle 3 is in a position away from the fixed handle 2. After the firing handle 3 is pressed, the firing handle 3 rotates to a position close to the fixed handle 2. The pin post 6 has a first state and a second state. When the pin post 6 is in the first state, the first end 61 of the pin post 6 enters the stopping groove 53, then the firing handle 3 cannot rotate relative to the actuating rod 5, so the limitation to a relative position relationship between the firing handle 3 and the actuating rod 5 is realized, and the stapler is in the insurance state. When the pin post 6 is in the second state, the first end 61 of the pin post 6 is separated from the stopping groove 53, and won't block the rotating action of the firing handle 3, and the stapler is in the ready-to-fire state. A button assembly 10 used for switching the states of the pin post 6 is provided at one side of the firing handle 3. The button assembly 10 is preferably provided at the side of the firing handle 3 away from the fixed handle 2, to facilitate the operation of the doctor. The button assembly 10 includes a pressing rod 71, and a first end of the pressing rod 71 is inserted in the firing handle 3. When the button assembly 10 is in its initial position and the firing handle 3 is pressed, the first end 61 of the pin post 6 enters the stopping groove 53. At this time, if the firing handle 3 is released, the firing handle 3 cannot return to its initial position under the function of the pin post 6. When the button assembly 10 is pressed towards the firing handle 3, the button assembly 10 moves as a whole, from its initial position towards the firing handle 3, so that the pressing rod 71 further enters the firing handle 3, the pressing rod 71 presses the pin post 6 to make the first end 61 of the pin post 6 move towards the second end 32 of the firing handle 3, then the pin post 6 enters the second state from the first state, that is, the first end 61 of the pin post 6 is separated from the stopping groove 53, and the firing handle 3 returns to its initial position under a function of a reset component at the same time.

Figure 17:
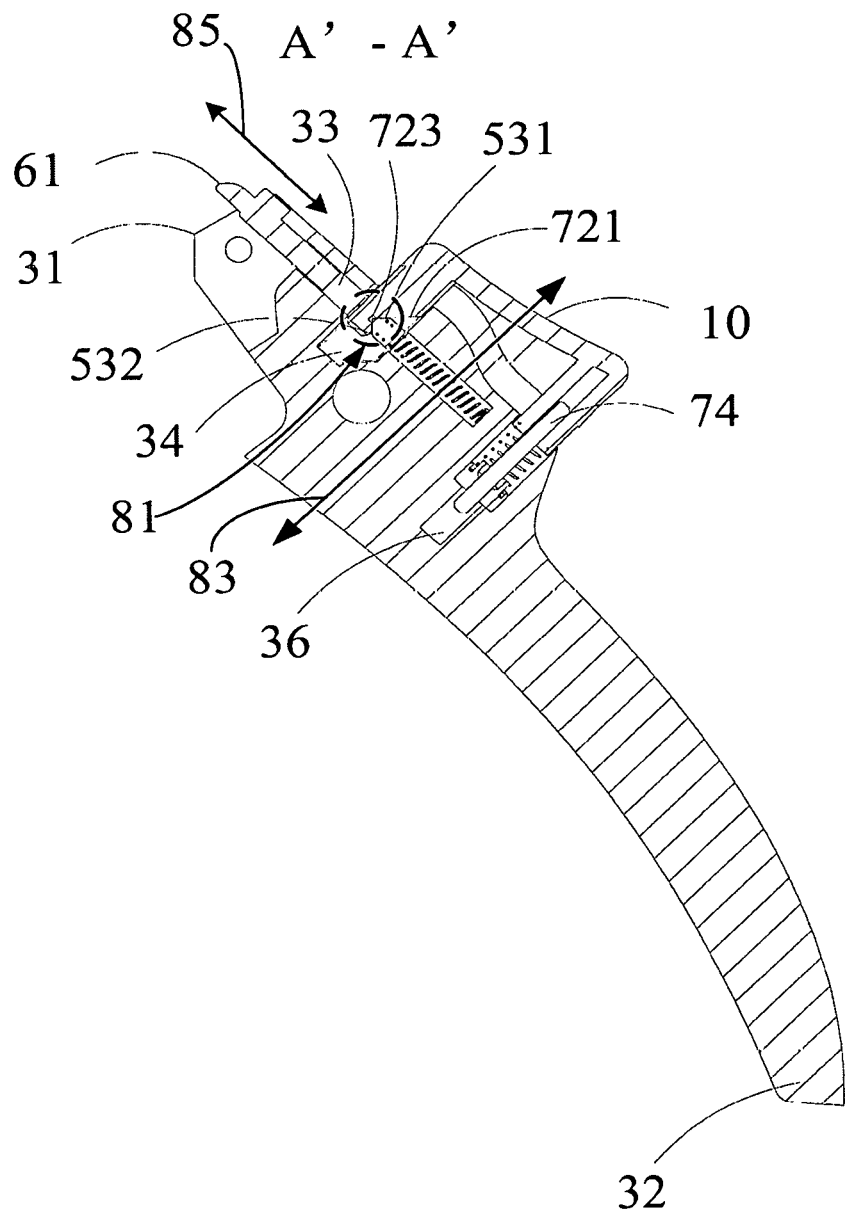
FIG. 17 is a section view along A'-A' direction of FIG. 16.

As shown in FIGS. 14-17, a pin groove 33 for accommodating the pin post 6 and a guiding groove 34 for accommodating the pressing rod 71 are provided in the firing handle 3. The pin groove 33 extends along a third direction 85, and the guiding groove 34 extends along a second direction 83, and the pin groove 33 and the guiding groove 34 cross each other. As shown in FIG. 17, the third direction approximately extends along a length direction of the firing handle 3, the second direction 83 is perpendicular to or approximately perpendicular to the third direction 85. The cross position between the pin groove 33 and the guiding groove 34 is a cooperation position between the first cooperating portion 63 of the pin post 6 and the second cooperating portion 72 of the pressing rod 71, the pressing rod 71 and the pin post 6 cross each other at the cross position of the two grooves, so the pressure can be passed from the pressing rod 71 towards the pin post 6. The pin post 6 can only move in a straight line, along the extending direction of the pin groove 33, to switch between the first state and the second state. The pressing rod 71 can only move along the extending direction of the guiding groove 34.

In the embodiment, the pin post 6 is provided with the first cooperating portion 63 having a first inclined surface 531. The first end of the pressing rod 71 is provided with the second cooperating portion 72 having a third inclined surface 721. When the pressing rod 71 is in its initial position, the third inclined surface 721 fits with the first inclined surface 531. When the pressing rod 71 further enters the firing handle 3 from its initial position, the first inclined surface 531 slides along the third inclined surface 721, so that the first end 61 of the pin post 6 moves towards the second end 32 of the firing handle 3. In the viewpoint of the FIG. 17, the first inclined surface 531 inclines upwards from the right side towards the left side. The inclined direction of the third inclined surface 721 is the same with the inclined direction of the first inclined surface 531, that is, inclining upwards from the right side towards the left side. When the pressing rod 71 further enters the firing handle 3 along a direction from the right side towards the left side, the third inclined surface 721 presses the first inclined surface 531 downwards, the first cooperating portion 63 drives the pin post 6 to move towards the second end 32 of the firing handle 3 as a whole.

Furthermore, the first cooperating portion 63 may further include a second inclined surface 532 located correspondingly to the first inclined surface 531. The second cooperating portion 72 may further include a fourth inclined surface 722 located correspondingly to the third inclined surface 721. When the pressing rod 71 is in its initial position, the fourth inclined surface 711 fits with the second inclined surface 532. In the viewpoint of FIG. 17, the second inclined surface 532 inclines upwards from the left side towards the right side, and the inclined direction of the fourth inclined surface 722 is the same with the inclined direction of the second inclined surface 532, that is, inclining upwards from the left side towards the right side.

As shown in FIG. 17, an intersection 81 between the first inclined surface 531 and the second inclined surface 532 protrudes towards the first end 61 of the pin post 6, a cavity 723 is formed at an intersection between the third inclined surface 721 and the fourth inclined surface 722. When the pressing rod 71 is in its initial position, the intersection between the first inclined surface 531 and the second inclined surface 532 enters the cavity 723. Therefore, when the button assembly 10 is not pressed, the first cooperating portion 63 and the second cooperating portion 72 cannot move relatively to each other, and the stability of the pressing rod 71 in its initial position when the button assembly 10 is not pressed is improved.

As shown in FIGS. 14-17, to better guide the button assembly 10 when being pressed and prevent the button assembly 10 from separating from the firing handle 3 when the pressing rod 71 is in the initial position, the button assembly 10 further may include a connecting portion 76 and a guiding rod 73. The guiding rod 73 is connected to the pressing rod 71 through the connecting portion 76. A button guiding groove 35 for accommodating the guiding rod 73 is provided in the firing handle 3, and a first end of the guiding rod 73 is inserted into the button guiding groove 35. In the embodiment, there are two guiding rods 73, there are also two button guiding grooves 35, and each guiding rod 73 is an elastic guiding rod. When the guiding rods 73 are in its initial state, a distance between the two guiding rods 73 when they are opened outwards is larger than a distance between the two button guiding grooves 35. When the button assembly 10 is mounted to the firing handle 3, the two guiding rods 73 are compressed towards the middle, to make the two guiding rods 73 elastically deform to a certain extent towards the middle, to ensure that the guiding rods 73 can be inserted into the two button guiding grooves 35. After the guiding rods 73 are inserted into the two button guiding grooves 35, under the returning force of the guiding rods 73, the guiding rods 73 can be kept in the two button guiding grooves 35. To further improve the stability of the guiding rod 73 and prevent the guiding rods 73 from accidently separating from the button guiding grooves 35, a clamping portion 731 is further provided at the first end of the guiding rod 73, and a sliding groove 341 for the clamping portion 731 is provided at a side surface of the button guiding groove 35. When the guiding rod 73 is inserted into the button guiding groove 35, the clamping portion 731 is inserted in the sliding groove 341, to limit the movement of the clamping portion 731. Therefore, the guiding rod 73 can only move in a straight line, along the extending direction of the button guiding groove 35. Under a clamping and stopping function of the clamping portion 731 in the button guiding groove 35, when the pressing rod 71 is in its initial position, the button assembly 10 won't be separated from the firing handle 3.

To realize the automatic reset of the button assembly 10 after being pressed, the button assembly 10 further includes a connecting portion 76 and a button shaft 74. The button shaft 74 is connected to the pressing rod 71 through the connecting portion 76, and a button shaft mounting groove 36 for accommodating the button shaft 74 is provided in the firing handle 3. A button reset spring 75 is provided in the button shaft mounting groove 36. When the button assembly 10 moves from its initial position towards the firing handle 3 to drive the pressing rod 71 to further enter the firing handle 3, the button reset spring 75 is deformed. After the external force applied on the button assembly 10 is released, the deformation returning force pushes the button assembly 10 to move away from the firing handle 3, to make the button assembly 10 return to its initial position. A shaft sleeve 37 is further provided in the button shaft mounting groove 36, the button shaft 74 passes through the shaft sleeve 74. Therefore, during the process of the button assembly 10 moving in the button shaft mounting groove 36, the button assembly 10 moves more smoothly.

Furthermore, to realize the automatic reset of the pin post 6, a pin post reset component is further provided between the second end 62 of the pin post 6 and the pin groove 33. The pin post reset component can be a pin post reset spring 7.

Figure 18:
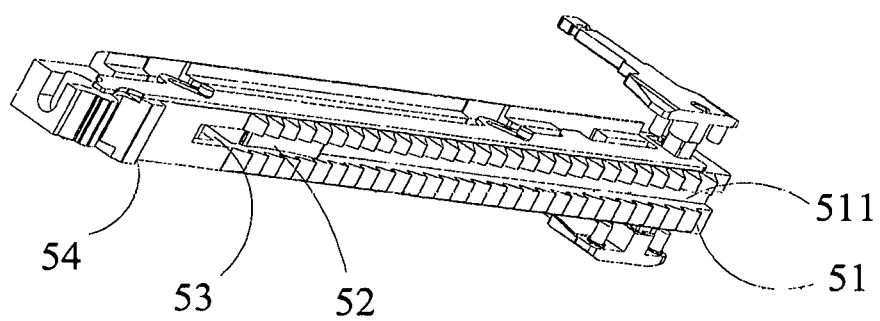
FIG. 18 is a stereogram of an actuating rod according to another embodiment of the present disclosure.
Figure 19:
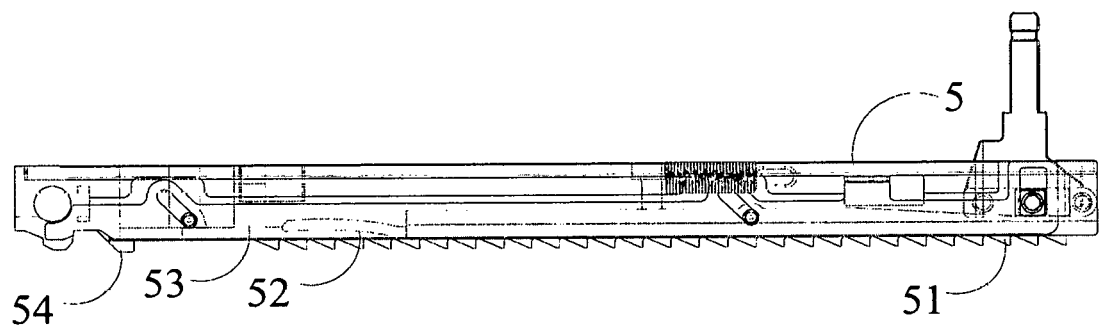
FIG. 19 is a structural schematic view of the actuating rod according to another embodiment of the present disclosure.

As shown in FIG. 18 and FIG. 19, a proximal end of the stopping groove 53 is provided with an arc groove 52 concave towards the inside portion of the actuating rod 5. When the firing handle 3 is pressed, the firing handle 3 rotates from its initial position towards the fixed handle 2, the arc groove 52 cooperates with the first end 61 of the pin post 6 and guides the first end 61 of the pin post 6 to enter the stopping groove 53, to prevent the interference between the first end 61 of the pin post 6 and the actuating rod 5 when they are in contact with each other, to make the first end 61 of the pin post 6 moves along the actuating rod 5 more smoothly.

In the present disclosure, positions of the distal end and the proximal end are defined relative to an operator, wherein, the proximal end is an end closer to the operator, the distal end is another end far from the operator and closer to a surgical position. For example, in the viewpoint of FIG. 13, a distal end of the instrument body 1 is the left end, and a proximal end of the instruments body 1 is the right end. In the viewpoint of FIG. 19, a distal end of the actuating rod 5 is the left end, and a proximal end of the actuating rod 5 is the right end.

Furthermore, the actuating rod 5 is further provided with a pushing tooth at the distal end side of the stopping groove 53, the pushing tooth 54 can cooperate with a driving component, in the embodiment, the driving component is a claw 4 provided at the firing handle 3, and the specific cooperation way will be described in detail in the following. The actuating rod 5 is further provided with a gear rack 51 at the proximal end side of the stopping groove 53, the gear rack 51 can cooperate with the claw 4 provided at the firing handle 3, and the specific cooperation way will be described in detail in the following. A middle portion of the gear rack 51 can be provided with a gear rack groove 511, to realize a receding effect to the first end 61 of the pin post, and the way of receding be described in detail in the following.

Figure 20:
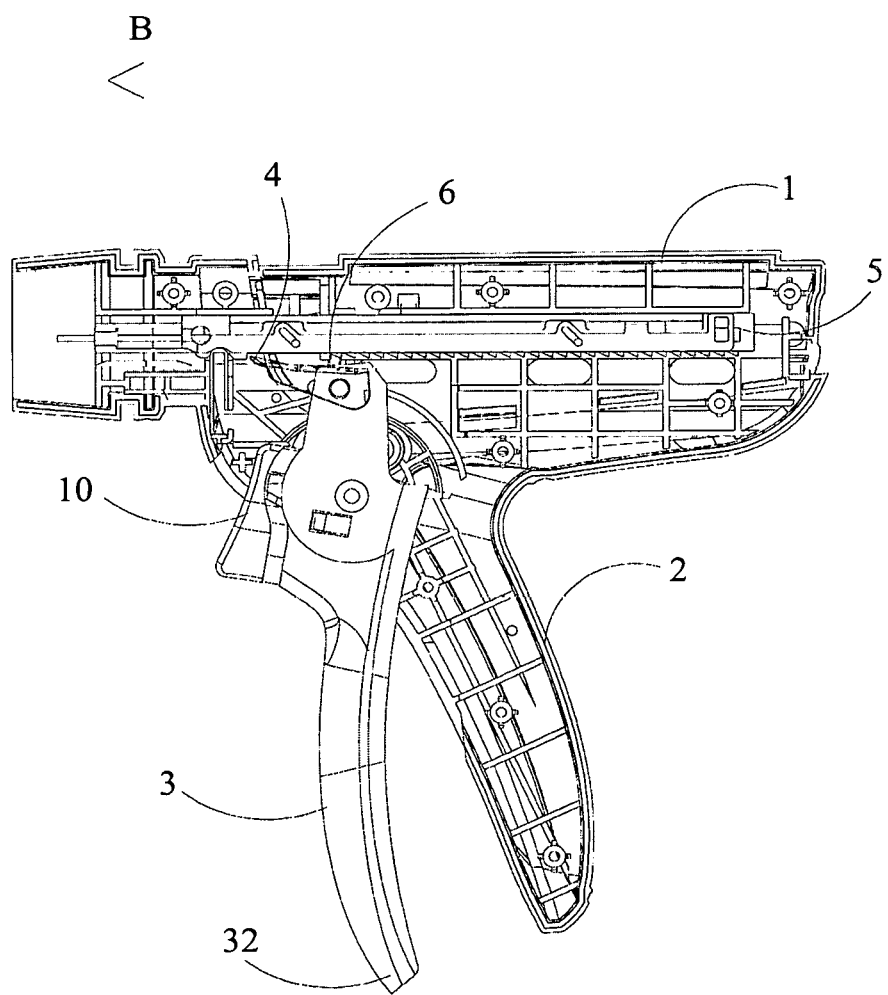
FIGS. 20-22 are structural schematic views of the firing handle according to another embodiment of the present disclosure.

In the following, the state of the firing mechanism when the pin post 6 is in the first state combining with FIG. 13, FIG. 20, and FIG. 21. FIG. 13 shows the structure of the stapler in the initial state. The pin post 6 and the firing handle 3 are both in the initial state, and the second end 32 of the firing handle 3 is away from the fixed handle 2. In the state shown in FIG. 13, the actuating rod 5 is in its initial position. At this time, if the firing handle 3 is pressed, the firing handle 3 rotates towards the fixed handle 2 to get close to the fixed handle 2, to enter the state shown in FIG. 20. In the embodiment, at this time the firing handle 3 is pressed, and the button assembly 10 is in its initial position. At this time, the claw 4 of the firing handle 3 is in contact with the pushing tooth 54 on the actuating rod 5 and pushes the pushing tooth 54 towards the distal end of the stapler, and the pushing tooth 54 drives the actuating rod 5 to move towards the distal end of the stapler, that is, the actuating rod 5 moves along the direction B shown in FIG. 20. Then the actuating rod 5 moves a displacement from the initial position of the actuating rod 5 towards the distal end of the stapler. At this time, under the function of the pin post reset spring 7, the first end 61 of the pin post 6 is guided by the arc groove 52 to enter the stopping groove 53 of the actuating rod 5 and enter the first state. At this time, even if the firing handle 3 is released, the firing handle 3 cannot return to its initial position under the limiting function of the pin post 6 and the stopping groove 53. At this time, the stapler cannot be fired and is in the insurance state.

Figure 21:
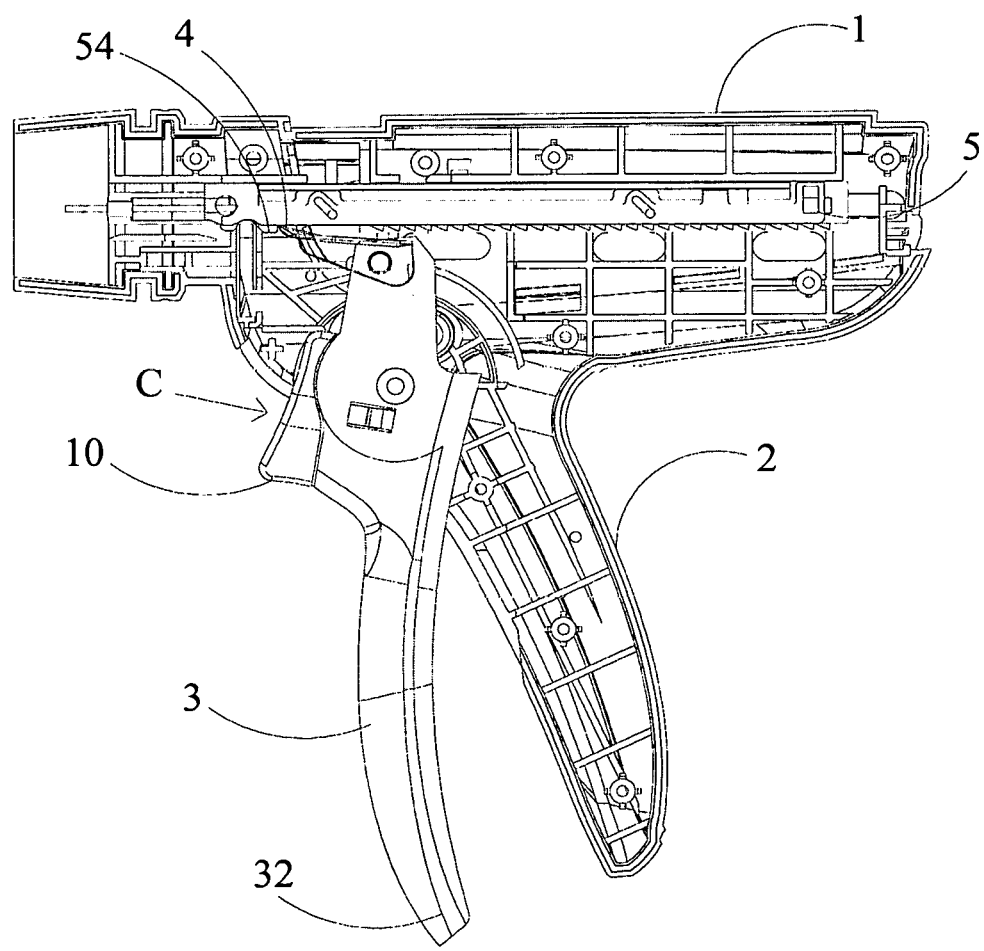
Figure 22:
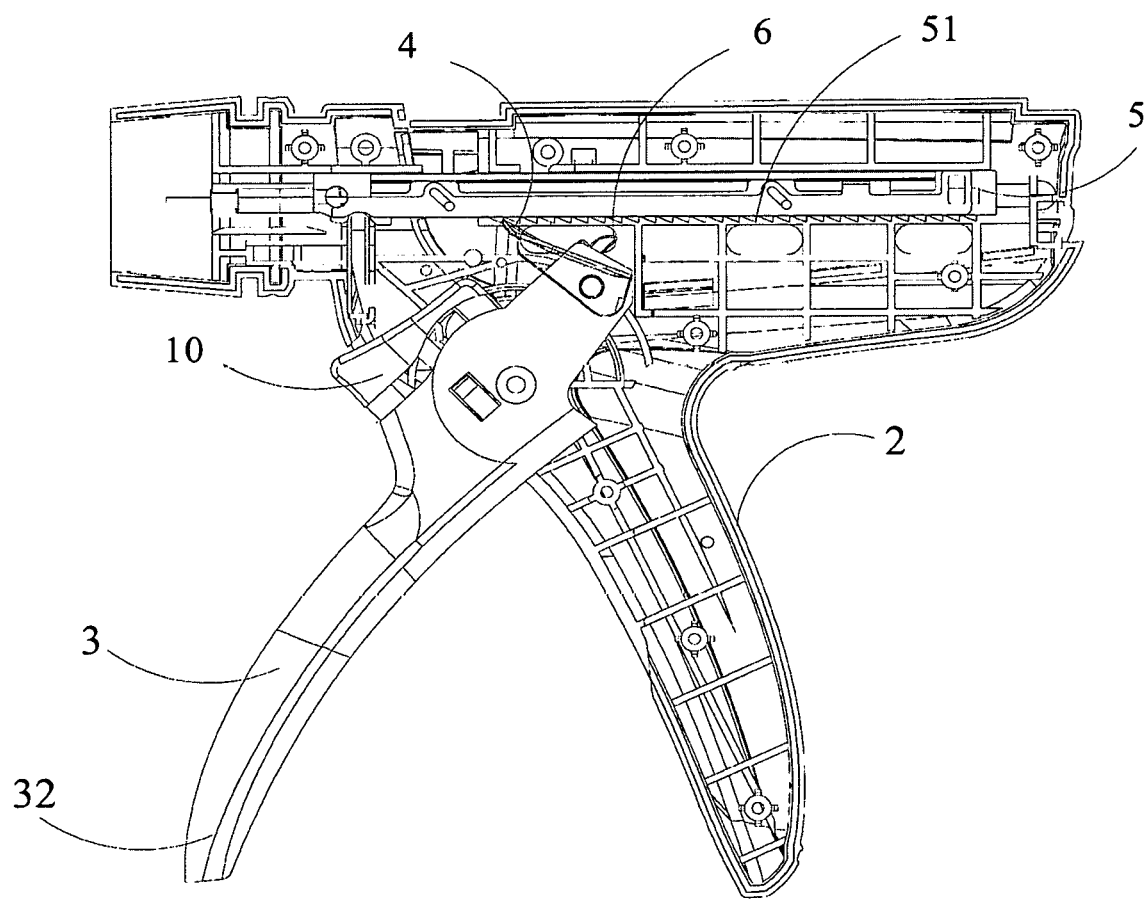

After the doctor completes the preparation of the operation, as shown in FIG. 21, in the embodiment, the firing handle is pressed, and the button assembly is pressed down. The button assembly 10 is pressed along the direction C shown in FIG. 21, the pressing rod 71 further enters the firing handle 3. Under the pressure from the pressing rod 71, the pin post 6 moves towards the second end 32 of the firing handle 3 and enters the second state from the first state, the first end 61 of the pin post 6 is separated from the stopping groove 53 and enters the state shown in FIG. 21. At this time, the firing handle 3 can rotate to return the initial position shown in FIG. 22 under the function of the reset component (such as a reset spring) for the firing handle 3, then the firing handle 3 returns to its initial state, and the button assembly is in its initial position. After the firing handle 3 returns to its initial position, the position of the claw 4 corresponds to the position of the gear rack 51 of the actuating rod 5. At this time, when the button assembly 10 is released, the button assembly 10 returns to its initial position under the function of the button reset spring 75. A reset component 7 for the pin post 6 is provided, in the embodiment, the reset component 7 is a pin post reset spring 7. Under the function of the pin post reset spring 7, the first end 61 of the pin post 6 moves away from the second end 32 of the firing handle 3 and protrudes from the first end 31 of the firing handle 3 again. If the doctor presses the firing handle 3 again, to make the firing handle 3 rotate towards the fixed handle 2, the first end 61 of the pin post 6 is in contact with the gear rack groove 511, and the gear rack groove 511 realizes the receding to the movement of the first end 61 of the pin post 6. Then the claw 4 of the firing handle 3 is in contact with the gear rack 51 and pushes the gear rack 51 to drive the actuating rod to move towards the distal end of the stapler, to fire the stapler.

The firing mechanism and the stapler of the present disclosure has the following advantages.

The present disclosure provides a firing mechanism for a stapler. The cooperation between the pin post and the actuating rod realizes the firing insurance mechanism. After the stapler is closed, the doctor needs to adjust the clamping state of the tissues in the staple head portion, for example flattens the tissues, to make the tissues to reach a ready-to-fire state. Before the tissues reach the ready-to-fire state, the pin post is inserted in the stopping groove of the actuating rod, to limit the rotation of the firing handle, then the driving component of the firing handle cannot push the actuating rod to move towards the actuating rod. The operator cannot press the firing handle to fire the stapler, to prevent the stapler from being fired before the operation is prepared. When the button assembly moves along the first direction, the pin post can be pressed to separate from the stopping groove and will not limit the rotating action of the firing handle, the firing handle can be rotated, so the driving component can push the actuating rod to fire the stapler. Besides, in another embodiment of the present disclosure, the position of the pin post can be switched by pressing the button assembly. The button assembly is provided at the firing handle and there is no need to specially provide a separate structure for carrying the button assembly, the doctor can operate the firing handle by only one hand, the button assembly is easy to operate, to facilitate the operation of the doctor. The stapler of the present disclosure is not limited to a linear stapler, but also can be other kinds of stapler.

The above is a detailed description of the present disclosure in connection with the specific preferred embodiments, and the specific embodiments of the present disclosure are not limited to the description. Modifications and substitutions can be made without departing from the spirit and scope of the present disclosure.

What is claimed is:

1. A firing mechanism for a stapler, wherein, the firing mechanism comprises:
    an actuating rod provided with a stopping groove;
    a firing handle, wherein a pin post is provided in the firing handle, the pin post is provided with a first end and a first cooperating portion, the first end of the pin post is capable of protruding from a first end of the firing handle and entering the stopping groove, to stop the firing handle from rotating relative to the actuating rod;
    a pressing button provided with a second cooperating portion and capable of rotating along a first direction to force the first end of the pin post to move towards a second end of the firing handle; and
    a balance block comprising a rotating portion and a connecting portion, wherein the connecting portion of the balance block is connected to the pressing button;
    wherein, when the firing handle is pressed in an initial state, the firing handle rotates from a second position to a first position, the stapler is closed, the first end of the pin post protrudes from the first end of the firing handle and enters the stopping groove, to stop the firing handle from rotating relative to the actuating rod;

when the firing handle is in the first position and the pressing button is pressed, the pressing button is rotated along the first direction with the rotating portion, the second cooperation portion presses the first cooperation portion, so that the pin post is pressed towards a second end of the firing handle, and the first end of the pin post is separated from the stopping groove.

2. The firing mechanism according to claim 1, wherein, a pin groove for accommodating the pin post is provided in the firing handle, and a reset component is provided between a second end of the pin post and the pin groove, so that the pin post is capable of moving in a straight line along a direction limited by the pin groove.

3. The firing mechanism according to claim 1, wherein, the first cooperating portion is a boss comprising a stopping portion and a step portion, and the second cooperating portion is a concave platform.

4. The firing mechanism according to claim 1, wherein, the pressing button comprises a pressing portion connected to the second cooperating portion, and the pressing portion passes through a housing of the stapler.

5. The firing mechanism according to claim 4, wherein, a limiting component for the pressing button is provided at a housing of the stapler, and the limiting component is located on a route of the pressing button moving along the first direction.

6. The firing mechanism according to claim 1, wherein, a proximal end of the stopping groove is provided with an arc groove concave towards an inside portion of the actuating rod.

7. A surgical stapler, comprising the firing mechanism according to claim 1.

* * * * *